United States Patent [19]

Pews et al.

[11] Patent Number: 5,239,105
[45] Date of Patent: Aug. 24, 1993

[54] CATALYTIC FORMATION OF DIARYLCARBONATES

[75] Inventors: R. Garth Pews; Robert G. Bowman, both of Midland, Mich.

[73] Assignee: The Dow Chemical Company, Midland, Mich.

[21] Appl. No.: 828,339

[22] Filed: Jan. 30, 1992

[51] Int. Cl.⁵ .............................................. C07C 68/00
[52] U.S. Cl. .................... 558/274; 544/357; 544/401
[58] Field of Search ................ 558/274; 544/357, 401, 544/402; 564/470

[56] References Cited

U.S. PATENT DOCUMENTS

| | | | |
|---|---|---|---|
| 2,362,865 | 11/1944 | Tryon et al. | 260/463 |
| 3,576,838 | 4/1971 | Urness et al. | 260/463 |
| 4,045,464 | 8/1977 | Romano et al. | 260/463 |
| 4,182,726 | 1/1980 | Illuminati et al. | 260/463 |
| 4,410,464 | 10/1983 | Hallgren | 260/463 |
| 4,487,962 | 12/1984 | Krabetz et al. | 562/531 X |
| 4,552,704 | 11/1985 | Mark | 260/463 |
| 4,609,501 | 9/1986 | Mark | 260/463 |
| 4,927,931 | 5/1990 | Molzahn et al. | 544/357 |
| 4,983,735 | 1/1991 | Hartwell et al. | 544/402 |
| 4,996,363 | 2/1991 | Bowman et al. | 564/470 |
| 5,034,557 | 7/1991 | Kiso et al. | 558/274 |
| 5,073,635 | 12/1991 | Bowman et al. | 544/401 |

OTHER PUBLICATIONS

Japanese Kokai No. 54,125,617 of Mitsubishi Chem. Ind. KK (Sep. 29, 1979).
Abrams, "Carbonic and Chloroformic Esters" *Kirk-Othmer Encyl. of Chemical Technology*, 3d Ed., John Wiley & Sons, Inc., vol. 4 (1978) pp. 758-771.
Matzner et al., "The Chemistry of Chloroformates" Chem. Rev., vol. 64 (1964), pp. 645-687 Kiso et al., in CA 112: 157845h (1990).
CA 98: 106998r of Asahi Chemical Industry Company (1983).
Derwent Abstract No. 07873C/05 (1987) of French Patent No. 2,422,621 to General Electric Co.
Derwent Abstract No. 83-729852/32 (1983) of DE 3,203,190 of Bayer AG.
Derwent Abstract No. 89-230848/32 of Japan Kokai, 165,551 of Asahi Chem. Ind. KK (1989).

*Primary Examiner*—Arthur C. Prescott
*Attorney, Agent, or Firm*—Robert M. O'Keefe

[57] ABSTRACT

Diphenylcarbonate is produced by contacting phenol with phosgene or phenylchloroformate or mixture thereof in the presence of one or more heterogeneous catalysts. The catalysts include Group VB metal oxides: silicates of Groups IIA, IIIB, IVB, VB, and the lanthanide and actinide metals: tungsten oxides: and clays. The more preferred catalysts are silicates of yttrium, titanium, or zirconium.

22 Claims, No Drawings

CATALYTIC FORMATION OF DIARYLCARBONATES

BACKGROUND OF THE INVENTION

This invention relates to a process for preparing diarylcarbonates, such as diphenylcarbonate.

The reaction of phenols with phosgene is well known in the prior art. In the reactions employing phosgene, a phenol is heated in the presence of a homogeneous catalyst such as an inorganic base, with or without a solvent. Next, the mixture is gassed with phosgene. If a one to one mole ratio of phenol to phosgene is used, the reaction produces the phenylchloroformate. But if two or more equivalents of the phenol are employed, the reaction yields a diarylcarbonate. These methods are not without difficulties, however, because the homogeneous catalyst must be separated from the product in another step. Moreover, it is known that traces of the catalyst remain in the product despite the great care placed in removing the contaminants. What is needed, therefore, is an efficient method of producing diarylcarbonates which alleviates these problems.

SUMMARY OF THE INVENTION

It has now been found that heterogeneous catalysts, insoluble in the reaction media, may be employed in the reaction of phosgene or arylchloroformates or mixtures thereof with phenols. The use of the heterogeneous catalysts of the present invention eliminates the necessity of chemically removing the homogeneous catalysts of the prior art from the products. Consequently, the products of the instant process are not contaminated with traces of catalyst. Since the catalysts of the present invention are insoluble in the reaction media, catalyst losses are minimized and the separation of products from the catalyst is relatively easy. Likewise, the ease of catalyst recovery provides economic advantages, such as a low cost of catalyst per amount of diarylcarbonate produced due to very low loss of catalyst. The use of the heterogeneous catalysts of the present invention provides high selectivity and a low percentage of by-products.

In one respect, the present invention is a process for the production of diarylcarbonates, comprising contacting phenol or substituted phenol with phosgene, an arylchloroformate, or a mixture of phenylchloroformate and phosgene in the presence of a heterogeneous catalyst under conditions effective for the formation of a diarylcarbonate, the heterogeneous catalyst being selected from the group consisting of:
(a) Group VB metal oxides:
(b) silicates of Groups IIA, IIIB, IVB, VB, and the lanthanide and actinide metals:
(c) tungsten oxides: and
(d) clays.

This invention, in another respect, is a process for the production of diphenylcarbonate, comprising the step of contacting phenol with phenylchloroformate, phosgene, or a mixture of phenylchloroformate and phosgene in the presence of a heterogeneous catalyst under conditions effective for the formation of a diphenylcarbonate, said heterogeneous catalyst being a silicate of yttrium, titanium, or zirconium.

The diarylcarbonates are useful in the production of polycarbonates.

DETAILED DESCRIPTION OF THE INVENTION

The phenols which can be used in the process of this invention comprise phenol and substituted phenols. The useful phenols are of the formula:

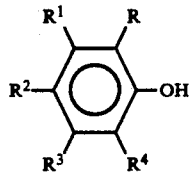

wherein R, R1, R2, R3, and R4 are separately in each occurrence hydrogen, halo, or alkyl, the alkyl being $C_1$–$C_{10}$, preferably $C_1$–$C_3$. Non-limiting examples of suitable substituted phenols are o-cresol, m-cresol, p-cresol, 4-tert-butylphenol, 4-ethylphenol, and 4-propylphenol. Unsubstituted phenol is most preferred.

The arylchloroformates useful in the present invention comprise the phenylchloroformate and the chloroformates of the above described substituted phenols. Thus, the arylchloroformates are of the formula:

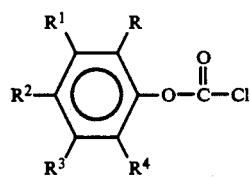

wherein R is separately in each occurrence hydrogen or alkyl, the alkyl being $C_1$–$C_{10}$, preferably $C_1$–$C_3$. Most preferably, the arylchloroformate is phenylchloroformate.

Phosgene is readily available commercially and can be used in pure form or diluted with an inert carrier gas such as nitrogen.

A. Group VB Metal Oxides

Group VB metal oxides are suitably employed as catalysts in the process of this invention. The Group VB elements include vanadium (V), niobium (Nb), and tantalum (Ta). Examples of suitable Group VB metal oxides include vanadium oxides such as VO, $VO_2$, $V_2O_3$, $V_2O_5$, $V_3O_5$, $V_5O_9$, $V_6O_{13}$; niobium oxides such as NbO, $NbO_2$, $Nb_2O_5$ tantalum oxides such as $Ta_2O_5$ as well as hydrated oxides including vanadates such as $H_3VO_4$, niobic acids such as $Nb_2O_5 \cdot xH_2O$, $H_8Nb_6O_{19} \cdot xH_2O$, and $[H_2Nb_6O_{16}]_m$, tantalic acid, and mixtures of Group VB metal oxides and/or hydrated metal oxides. Non-stoichiometric oxides are also suitable. Preferably, the Group VB metal is in the +3 or +5 oxidation state. More preferably, the Group VB metal oxide is an oxide or hydrated oxide of niobium. Most preferably, the Group VB metal oxide is a hydrated niobium oxide.

Generally, the common Group VB metal oxides are commercially available: while the less common oxides can be prepared by methods known in the art. The preparation of some less common Group VB metal oxides can be found in *Comprehensive Inorganic Chemistry*, op. cit., pp. 510–524 and 592–599.

B. Silicates of Groups IIA, IIIB, IVB, VB, and the Lanthanide and Actinide Metals Metal silicates are suitably employed as catalysts in the process of the present invention. The metal silicate is any silicate of Groups IIA, IIIB, IVB, VB, and the lanthanide and actinide metals. Preferably, the metal of the metal silicate is beryllium, magnesium, calcium, strontium, barium, actinium, thorium, protactinum, uranium, scandium, yttrium, lanthanum, titanium, zirconium, hafnium, vanadium, niobium, or tantalum. More preferably, the metal of the metal silicate is magnesium, titanium, niobium, zirconium, or yttrium. Most preferably, the metal of the metal silicate is yttrium, zirconium, or titanium. The metal silicate can be employed in an amorphous form containing a distribution of silicate anions of various sizes. Alternatively, the metal silicate can be employed in a crystalline form, such as the siliceous zeolite structure exhibited by sodium magnesium silicate.

The mole ratio of silicon to metal will vary in the metal silicate depending upon the metal cation, its valence, and the form of the silicate anion. For instance, in the case of magnesium silicate, the preferred silicon to magnesium mole ratio varies from about 0.5 to about 20. More preferably, the silicon to magnesium mole ratio varies from about 1 to about 10, most preferably, from about 1 to about 5. Other metal silicates may exhibit silicon to metal mole ratios which are different from the preferred ratios shown here for magnesium silicate.

The common metal silicates which are employed in the process of this invention are commercially available. The less common silicates, such as thorium silicate and other metal silicates, may be prepared by methods reported in *The Colloid Chemistry of Silica and Silicates* by Ralph K. Iler, Cornell University Press, 1955: or in *The Chemistry of Silica: Solubility, Polymerization, Colloid and Surface Properties, and Biochemistry* by Ralph K. Iler, John Wiley & Sons, 1979: and references therein.

The metal silicate catalyst can be prepared by a variety of synthetic methods. One, for example, requires the formation of a mixture of silica ($SiO_2$) with the oxide of the desired metal. The oxide mixture is calcined at a temperature sufficient to form the desired metal silicate. Another method, for example, depends upon the hydrolysis of mixtures of tetra(ethoxy)silicon and an alkoxide of the desired metal, e.g., tetra(methoxy)titanium. The hydrolysis reaction yields the desired metal silicate. Preferably, however, the metal silicates are prepared by direct precipitation from a mixture of two aqueous solutions. One of these solutions contains a soluble silicate salt, such as sodium silicate. Typically, the soluble silicate salt is dissolved in a minimum amount of water. Typically, the solution is heated, preferably to boiling, to aid in the dissolution of the salt. Optionally, the aqueous silicate solution can be acidified with strong acid, such as nitric acid, in order to prepare larger silicate anions, such as $Si_2O_5^{2-}$ or $Si_3O_7^{2-}$. Similarly, a soluble metal compound containing the desired metal ion is dissolved in a minimum amount of water to make a second solution. The soluble metal compound can be, for example, a metal nitrate, such as magnesium nitrate or lanthanum nitrate: a metal chloride, such as yttrium chloride: or the like. Likewise, the second solution is heated to boiling to facilitate dissolution of the soluble metal compound. The two solutions are mixed and a precipitate forms of the desired metal silicate catalyst. The catalyst is filtered and dried by known methods.

C. Tungsten Oxides

Tungsten oxides are also suitably employed in the process of this invention. The tungsten oxides can be simple mononuclear tungsten oxides, which are compounds containing only one tungsten atom, such as ammonium tungstate. Alternatively, the tungsten oxides can be multinuclear tungsten clusters, which are compounds containing a plurality of tungsten atoms, such as $(NH_4)_{10}(W_{12}O_{41})$. In addition, it is preferred that the tungsten be in the +4, +5, or +6 oxidation state. Examples of suitable tungsten oxides include $WO_2$, $WO_3$, $(NH_4)_2WO_4$, para-ammonium tungstate, $H_2(W_6O_{19})$, $[(n-C_4H_9N]_2(W_6O_{19})$, $(NH_4)_{10}(W_{12}O_{41})$, $(NR_4)_2(W_6O_{19})$ and $(NR_4)_4(W_{10}O_{32})$, wherein R is H or an alkyl moiety: however, the tungsten oxides are not limited to only the aforementioned examples. The preferred mononuclear tungsten oxide is $(NH_4)_2WO_4$. The preferred multinuclear tungsten oxide compounds have the general formula:

$$C_{2+w}[M_wW_{6-w}O_{19}]$$

wherein C is a monovalent cation, such as $Na^+$, $K^+$, $H^+$, or a quaternary ammonium salt, $NR_4^+$, wherein R is H or an alkyl moiety such as butyl or propyl, w is an integer from 0 to 3, and M is vanadium (V), niobium (Nb), or tantalum (Ta). Preferably, C is tetrabutylammonium (+1).

The more common of the tungsten oxides, such as $WO_2$, $WO_3$, $(NH_4)_2WO_4$, and para-ammonium tungstate can be purchased commercially. The less common oxides and cluster compounds can be prepared by methods described in *Comprehensive Inorganic Chemistry*, Vol. 3, J. C. Bailar, Jr., H. J. Emeleus, R. Nyholm, and A. F. Trotman-Dickenson, eds., Pergamon Press Ltd., Oxford (1973) pp. 763-769: and in "Isopolytungstates," by D. L. Kepert in *Progress in Inorganic Chemistry*, Vols. 4, Intersciences Press, New York (1962) p. 199. The preparation of $[(n-C_4H_9)_4]_2(W_6O_{19})$ and various polyoxometalates is reported by M. Filowitz, R. K. C. Ho, W. G. Klemperer, and W. Shum in *Inorganic Chemistry*, 18. no.1, 93-103 (1979), and by V. W. Day, W. G. Klemperer, and C. Schwartz in the Journal of the *American Chemical Society*, 109, No. 20, 6030-6044 (1987).

It is preferred that the aforementioned catalysts are insoluble in the reaction mixture, thereby acting as heterogeneous catalysts. Optionally, any of the catalysts can be made insoluble by (a) depositing onto a support material, or (b) binding with a refractory metal oxide or a support precursor. Suitable supports or binders include carbon and any refractory oxide such as alumina (hydrated and dehydrated forms), silica, zirconia, thoria, magnesia, titania, kieselguhr, and mixtures of these materials. Suitable support precursors include hydrated metal oxides and metal alkoxides. Preferably, the support or binder material is alumina, silica, or titania. The support material typically has a surface area of at least about 0.1 $m^2$/g. Preferably, the support material has a surface area in the range from about 5 $m^2$/g to about 600 $m^2$/g, most preferably in the range from about 50 $m^2$/g to about 200 $m^2$/g. These surface areas are measured by the Brunauer-Emmett-Teller (BET) method, as described by R. B. Anderson, in *Experimental Methods in Catalytic Research*, Academic Press (1968) pp. 48-66.

The catalyst compounds can be deposited onto the support material in any known fashion, such as by impregnation or by precipitation in situ from the catalyst preparation reaction. In these types of preparation the catalyst is adsorbed onto the support. Alternatively, the catalyst can be chemically reacted onto the support. In this method a catalyst precursor compound is reacted with the hydroxyl functionalities of the support to yield a catalyst precursor chemically bound to the support. The bound catalyst precursor can then be converted into the Group VB or VIB metal oxide catalyst by hydrolysis or heating. For example, niobium chloride reacts with the hydroxyl moieties of silica to yield niobium chloride bound through an oxygen to silicon. The bound niobium chloride can be heated in air or water vapor to yield a bound niobium oxide catalyst.

D. Clays

The catalyst of the present invention also comprises various clays. Many clays are widely available commercially. Non-limiting examples of suitable clays include montmorillonite and pillared clay. Pillared clay is defined as being clay having one or more metal oxygen clusters interdisposed between clay layers, thus enabling the layers to be separated even when dried. Such examples include $ZrO_2$ and $Al_2O_3$ pillared clays as described in U.S. Pat. No. 4,248,739 and U.S. Pat. No. 4,216,188, incorporated herein by reference.

The process of the present invention may be run batch-wise or in a continuous process wherein phosgene or arylchloroformate and the phenol or substituted phenol are intimately admixed through a heterogeneous catalyst bed as in a fluid bed reactor, for example. The process of this invention can be conducted in any suitable reactor, including batch reactors, fixed-bed reactors, slurry reactors, fluidized bed reactors, and catalytic distillation reactors. The reaction can be run in the gas phase, preferably at a temperature above the boiling point of the phenol. The amount of catalyst employed in the process will depend on various factors such as the concentration of the reactants, the temperature and pressure, and other variables known to those skilled in the art.

The amount of one or more catalysts described above, which is employed in the process of this invention is any amount which is effective in producing the desired diarylcarbonate products. The amount of catalyst varies widely depending upon the specific reactants and process conditions employed. Typically, for a batch reaction the quantity of catalyst is in the range from about 0.1 weight percent to about 20 weight percent based on the weight of reactants. Preferably, the amount of catalyst for a batch reaction is in the range from about 1 weight percent to about 15 weight percent based on the weight of reactant.

The catalyst can be regenerated, when needed, by well known methods such as by contacting the catalyst with a moving stream of oxygen-containing gas, such as air, at an elevated temperature.

Although it is preferred to carry out the process in the absence of solvent, it is within the scope of the invention for a solvent to be used, if desired, and especially if the substituted phenol has a high melting point. Any solvent is acceptable provided that it is not reactive with the reactants and diarylcarbonate products and it does not decompose under the conditions of the reaction. Some examples of suitable solvents include saturated aliphatic hydrocarbons such as pentane, hexane, octane, nonane, and decane, and aromatic hydrocarbons such as benzene, toluene, and xylene. The amount of solvent employed in the reaction depends on the particular reactants and reaction conditions. Any amount of solvent is acceptable that meets the intended purpose of use. Typically, the solvent constitutes from about 1 weight percent to about 95 weight percent of the feed stream. Preferably, the solvent constitutes from about 10 weight percent to about 80 weight percent of the feed stream.

The phenol or substituted phenol is contacted with an arylchloroformate, phosgene, or mixture thereof, in the presence of the catalyst at any operable temperature which promotes the formation of diarylcarbonate and produces the desired diarylcarbonate products. Typically, the temperature is in the range from about 20° C. to about 350° C. Preferably, the temperature is in the range from about 100° C. to about 300° C. More preferably, the temperature is in the range from about 125° C. to about 200° C. Below the preferred lower temperature the conversion may be low. Above the preferred upper temperature the selectivity for diarylcarbonates may decrease.

Likewise, the phenol or substituted phenol is contacted with an arylchloroformate, phosgene, or mixture thereof, in the presence of the catalyst at any operable pressure which promotes the reaction and produces the desired diarylcarbonate products. Preferably, the pressure is sufficient to maintain the reactants in the liquid state at the temperature of the reaction. More preferably, the pressure is in the range from about atmospheric to about 4000 psig. In batch reactors the pressure is autogenous, and depends upon the vapor pressures of the reactants and products and the temperature of the reaction.

When the process of this invention is conducted in a batch reactor, the reaction time determines the length of contact between the reactants and the catalyst. Any reaction time which yields the desired diarylcarbonate products is acceptable. The reaction time depends upon the quantity of reactants, the quantity of catalyst, the temperature of the reaction and desired degree of conversion. Preferably, the reaction time in a batch reactor is in the range from about 0.1 hour to about 20 hours.

When this invention is conducted in a continuous manner, the contact time is determined by the flow rate of the feed through the catalyst bed. Typically, the flow rate is from 0.01 to 100 bed volumes of reactants per hour. A skilled artisan can adjust the flow rate to maximize productivity. Such adjustments can be based on several factors such as type and amount of catalyst, concentration of reactants in feed, and temperature.

In a batch reactor, reaction products can easily be separated from the catalyst by conventional methods such as filtration. In a continuous process, the separation occurs continuously using conventional means. The products of this process can be further purified using conventional techniques such as distillation.

For the purposes of this invention, "conversion" is defined as the percentage of starting material, whether arylchloroformate or phosgene or both, which is converted to diarylcarbonate. The conversion varies widely depending upon the reactants, the form of the catalyst, and the process conditions, such as temperature, pressure, and flow rate. Within the preferred temperature range, as the temperature increases the conversion generally increases. Within the preferred space velocity range, as the space velocity increases the conversion generally decreases. Typically, the conversion is at least about 5 percent. Preferably, the conversion is at least about 10 percent: more preferably at least about 25 percent.

Typically, the process of this invention achieves high selectivities to diarylcarbonates. Within the preferred temperature range as the temperature increases, the selectivity for diarylcarbonates generally decreases.

The following examples are illustrative of the invention but are not intended to be limiting thereof. All percentages are given in weight percent unless noted otherwise.

EXAMPLE 1

Preparation of $Nb_2O_5$

Niobic Acid, $Nb_2O_5 \cdot xH_2O$ (Niobium Products Corp., CBMM number AD 222) is dried and heated slowly under air to a temperature of 300° C. and calcined overnight at that temperature.

EXAMPLE 2

Preparation of Titania-Supported Ammonium Tungstate

Para-ammonium tungstate (15.0 g: Amends Chemical Company) is added to 400 ml of water to which 5 ml of 30 percent hydrogen peroxide are added. The resulting mixture is heated with stirring at 80° C-90° C. for 60 minutes to form a solution. The solution is cooled to room temperature and added to a flask containing titania (25.0 g: titanium oxide: Saki Cs200). Water is removed by rotary evaporation. The resulting solid is dried in a muffle furnace at 300° C. overnight to form a titanium-supported tungsten oxide catalyst.

EXAMPLE 3

Preparation of Magnesium Silicate Catalyst

A first solution is prepared by dissolving $Na_2SiO_3 19$ $9H_2O$ (111.3g) in 1200 ml of water and heating to 80° C. The solution is heated to boiling and the volume is raised to 2000 ml by the addition of water. A second solution is prepared by dissolving $Mg(NO_3)_2 \cdot 6H_2O$ (100.0 g) in 2000 ml of water. The second solution is heated to boiling, whereupon the first solution is added at a rate of 100 ml/min to the second solution with rapid stirring. A precipitate forms. The supernatant and the precipitate are heated and stirred for about 3 hours at boiling, then cooled to room temperature overnight. The precipitate is filtered, washed three times with 2000 ml of water, and refiltered. The filtercake is dried at 100° C. to yield a magnesium silicate catalyst of approximate formula $MgOSiO_3$ or $MgO \cdot SiO_2$. The catalyst is calcined at 300° C. or 550° C. prior to use.

EXAMPLE 4

Preparation of Metal Silicate Catalysts

A series of metal silicate catalysts is prepared according to the following general procedure: $Na_2SiO_3 \cdot 9H_2O$ is dissolved in 1200 ml of water and heated to 80° C. Concentrated nitric acid is slowly added to the solution so that no precipitate forms during the addition. The acidified silicate solution is heated to boiling and the volume is raised to 2000 ml with water. In a separate flask a metal nitrate or metal chloride salt is dissolved in 2000 ml of water and heated to boiling. The acidified silicate solution is added hot at a rate of 100 ml/min to the nitrate solution with rapid stirring. A precipitate forms. The supernatent and the precipitate are heated and stirred for about 3 hours at boiling, then cooled overnight at room temperature. The cooled mixture is filtered, and the precipitate is washed with about 2000 ml of water and refiltered. The washing procedure is repeated twice more, and the resulting filtercake is dried at 100° C. overnight. The dried filtercake is calcined under air at 300° C. or 550° C. over a second night to yield a metal silicate catalyst, which is employed in the reforming process of this invention. Table I lists the kind and quantity of metal salts used in preparing the nitrate or chloride solutions, the quantities of nitric acid and sodium silicate used in making the sodium silicate solution, and the approximate formula of the resulting metal silicate catalyst.

TABLE I

| EX. | Metal Salt (g) | $Na_2SiO_3 \cdot 9 H_2O$ (g) | $HNO_3$ (ml) | Approx. Formula |
|---|---|---|---|---|
| 4(a) | $Mg(NO_3)2.6 H_2O$ | 222.5 g | 49 | $MgSi_2O_5$ or $MgO.2 SiO_2$ |
| 4(b) | $Mg(NO_3)2.6 H_2O$ | 222.7 g | 99 ml[1] | $MgSi_4O_9$ or $MgO.4 SiO_2$ |
| 4(c) | Davison Chemical Silica Magnesia SMR-55010384 | | | $MgO.xSiO_2$ |
| 4(d) | Reagent Chemical & Research, Inc. MAGNESOL ® Grade 30/40 | | | $MgO.xSiO_2$ |
| 4(e) | $La(NO_3)3.6 H_2O$ | 213.2 g | 48.5 ml | $La_2(Si_2O_5)_3$ or $La_2O_3.6 SiO_2$ |
| 4(f) | $(NH_4)2 Ce(NO_3)_6$ | 571.7 g | 131 ml | $Ce_2(Si_3O_7)_2$ or $CeO_2.6 SiO_2$ |
| 4(g) | $NbCl_5$ | 200.0 g | 0 ml | $Nb_2O_5.5 SiO_2$ |
| 4(h) | $Ga(NO_3)_3.9 H_2O$ | 289.0 g | 63 ml | $Ga(Si_2O_5)_3$ or $Ga_2O_3.6 SiO_2$ |
| 4(i) | $YCl_3.6 H_2O$ | 150.4 g | 33 ml | $Y_2(Si_2O_5)_3$ or $Ga_2O_3.6 SiO_2$ |
| 4(j) | $ZrOCl_2.4 H_2O$ | 228.0 g | 50 ml | $ZrOSi_2O_5$ or $ZrO_2.2 SiO_2$ |
| 4(k) | Titanium Silicate (30.7% $TiO_2$) commercial grade | | (30.7% $TiO_2$) | $TiO_2.3 SiO_2$ |

[1]10 ml in $Mg^{2+}$ solution and 89 ml in $SiO_3^{2-}$ solution

EXAMPLE 5

Preparation of Clays

Montmorillonite clay is obtained from a commercial vendor and calcined at about 300° C. prior to use.

Alumina pillared montmorillonite clay is prepared by adding 91.1 grams of a 50 percent chlorhydrol solution ("$Al_2(OH)_5Cl$" in water) to water and raising the amount of water to about 1400 cc. This solution is heated at 96° C. for 1.25 hours. Next, 100 cc of 0.30 M NaOH is added dropwise to the chlorhydrol solution. Then, 65.9 grams of of Na montmorillonite is added to the hot solution and is stirred at 96° C. for about one hour. The product is collected by centrifugation and then is washed until a pH of about 7 is obtained and no chlorine ion is detected. The resulting alumina pillared montmorillonite clay is dried at about 130° C. and then is calcined at about 300° C. prior to use.

EXAMPLE 6
Preparation or Diphenylcarbonate Over Several Heterogeneous Catalysts At 165° C., 0.1 mole phenol is contacted with 0.1 mole phenylchloroformate in the presence of the catalysts described in Table II as prepared by the procedures above. Samples were removed after the times indicated in Table II and analyzed by gas chromatography. The results of each analysis is reported in area percent. In Table II, "DPC" means diphenylcarbonate.

TABLE II

| Catalyst | Prep. Ex. | Time (Min.) | Area % $C_6H_5OH$ | $C_6H_5OCOCl$ | DPC |
|---|---|---|---|---|---|
| $Nb_2O_5$ | 1 | 10 | 40 | 51 | 9 |
|  |  | 30 | 35 | 44 | 21 |
| $WO_3/TiO_2$ | 2 | 20 | 40 | 52 | 7 |
|  |  | 60 | 24 | 30 | 45 |
| $MgOSiO_2$ | 3 | 45 | 37 | 50 | 13 |
|  |  | 75 | 34 | 45 | 21 |
|  |  | 120 | 29 | 36 | 35 |
| $MgSi_2O_5$ | 4a | 30 | 42 | 50 | 8 |
|  |  | 60 | 41 | 48 | 11 |
|  |  | 120 | 40 | 44 | 15 |
| $MgSi_4O_9$ | 4b | 30 | 38 | 48 | 14 |
|  |  | 60 | 28 | 34 | 38 |
|  |  | 120 | 19 | 22 | 59 |
| Silica-Magnesia | 4c | 30 | 44 | 53 | 9 |
|  |  | 60 | 30 | 41 | 29 |
| MAGNESOL 30/40 | 4d | 30 | 38 | 53 | 9 |
|  |  | 60 | 35 | 49 | 16 |
| $La_2(Si_2O_5)_3$ | 4e | 30 | 42 | 55 | 3 |
|  |  | 90 | 41 | 53 | 6 |
| $Ce(Si_2O_5)_2$ | 4f | 30 | 38 | 50 | 12 |
|  |  | 60 | 37 | 47 | 16 |
|  |  | 120 | 35 | 42 | 23 |
| $Nb_2O_5SiO_2$ | 4g | 10 | 38 | 51 | 11 |
|  |  | 30 | 35 | 45 | 20 |
| $Ga(Si_2OP_5)_3$ | 4h | 30 | 40 | 51 | 9 |
| $Y_2(Si_2O_5)_3$ | 4i | 30 | 6.5 | 4.5 | 89 |
|  |  | 60 | 5 | 2 | 94 |
| $ZrO(Si_2O_5)$ | 4j | 10 | 13 | 10 | 77 |
|  |  | 25 | 7 | 1 | 92 |
| $TiO_2SiO_2$ | 4k | 15 | — | — | >95 |
| Montmorillonite Clay | 5a | 60 | 20 | 24 | 56 |
|  |  | 120 | 10 | 11 | 89 |
|  |  | 240 | 5 | 3 | 92 |
| Pillared Clay | 5b | 30 | 15 | 15 | 70 |

It can be seen from the data in Table II that several heterogeneous catalysts are useful in the production of diarylcarbonates.

EXAMPLE 7
Preparation of Diphenylcarbonate Over Silicates of Zirconium, Titanium, and Yttrium The general procedure of Example 6 is repeated except the temperature is 150° C. and the catalysts are only those indicated in Table III. In Table III, phenyloctane was utilized as an internal standard: hence, the data for the conversion is reported in mole percent.

TABLE III

| Catalyst | Prep. Ex. | Time (Min.) | Mole % $C_5H_5OH$ | $C_6H_5OCOCl$ | DPC | Conv. |
|---|---|---|---|---|---|---|
| $ZrOSi_2O_5$ | 4j | 0 | 0.100 | 0.101 | 0.006 | 0 |
|  |  | 20 | 0.099 | 0.084 | 0.014 | 14 |
|  |  | 40 | 0.067 | 0.061 | 0.045 | 46 |
|  |  | 60 | 0.024 | 0.044 | 0.064 | 64 |
| $Y_2Si_2O_5$ | 4i | 0 | 0.088 | 0.087 | 0.000 | 0 |
|  |  | 20 | 0.083 | 0.078 | 0.018 | 19 |
|  |  | 40 | 0.054 | 0.050 | 0.045 | 46 |
|  |  | 60 | 0.039 | 0.035 | 0.058 | 60 |
| $TiO_2Si_2O_5$ | 4k | 0 | 0.106 | 0.106 | 0.000 | 0 |
|  |  | 20 | 0.025 | 0.009 | 0.086 | 81 |
|  |  | 40 | — | — | 0.104 | 98 |

What is claimed is:

1. A process for the production of diarylcarbonates, comprising contacting phenol or substituted phenol with phosgene, an arylchloroformate, or a mixture of arylchloroformate and phosgene in the presence of a heterogeneous catalyst under conditions effective for the formation of a diarylcarbonate, the heterogeneous catalyst being selected from the group consisting of:
   (a) Group VB metal oxides:
   (b) silicates of Groups IIA, IIIB, IVB, VB, and the lanthanide and actinide metals;
   (c) tungsten oxides: and
   (d) clays.

2. The process of claim 1 wherein the heterogeneous catalyst is a silicate of zirconium, yttrium, or titanium.

3. The process of claim 1 wherein the heterogeneous catalyst is a silicate of titanium.

4. The process of claim 1 wherein the temperature is from about 100° C. to about 300° C.

5. The process of claim 1 wherein the temperature is from about 125° C. to about 200° C.

6. The process of claim 1 wherein the substituted phenol is of the formula:

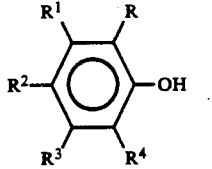

wherein R, $R^1$, $R^2$, $R^3$, and $R^4$ are separately in each occurrence hydrogen, halo, or alkyl of from 1 to 10 carbon atoms.

7. The process of claim 6 wherein R, $R^1$, $R^2$, $R^3$, and $R^4$ are separately in each occurrence hydrogen or alkyl of from one to three carbon atoms.

8. The process of claim 6 wherein R, $R^1$, $R^2$, $R^3$, and $R^4$ are hydrogen in each occurrence.

9. The process of claim 1 wherein the arylchloroformate is of the formula:

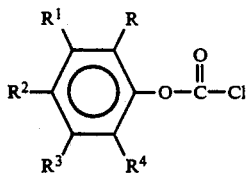

wherein R, $R^1$, $R^2$, $R^3$, and $R^4$ are separately in each occurrence hydrogen, halo, or alkyl of from 1 to 10 carbon atoms.

10. The process of claim 9 wherein R, $R^1$, $R^2$, $R^3$, and $R^4$ are separately in each occurrence hydrogen or alkyl of from one to three carbon atoms.

11. The process of claim 9 wherein R, $R^1$, $R^2$, $R^3$, and $R^4$ are is hydrogen in each occurrence.

12. The process of claim 1 wherein the pressure is in the range from about atmospheric to about 4000 psig.

13. The process of claim 1 wherein the process is carried out as a batch reaction.

14. The process of claim 1 wherein the process is carried out in a continuous manner.

15. A process for the production of diphenylcarbonate comprising contacting phenol with phenylchloroformate, phosgene, or a mixture of phenylchloroformate and phosgene in the presence of a heterogeneous catalyst under conditions effective for the formation of a diphenylcarbonate, said heterogeneous catalyst being a silicate of yttrium, titanium, or zirconium.

16. The process of claim 15 wherein the temperature is from about 100° C. to about 300° C.

17. The process of claim 15 wherein the temperature is from about 125° C. to about 200° C.

18. The process of claim 15 wherein the catalyst is a silicate of titanium.

19. The process of claim 15 wherein the pressure is in the range from about atmospheric to about 4000 psig.

20. The process of claim 15 wherein the process is carried out as a batch reaction.

21. The process of claim 15 wherein the process is carried out in a continuous manner.

22. The process of claim 21 wherein flow rate is from 0.01 to 100 bed volume of phenol per hour and temperature is from about 125° C. to about 300° C.

* * * * *